United States Patent [19]

Ohno et al.

[11] 4,268,496

[45] May 19, 1981

[54] SUSTAINED-RELEASE SOLID PHARMACEUTICAL DOSAGE FORMS AND PREPARATION THEREOF

[75] Inventors: Shigeru Ohno, Kamakura; Fujio Sekigawa, Omiya, both of Japan

[73] Assignee: Shin-Etsu Chemical Co. Ltd., Tokyo, Japan

[21] Appl. No.: 138,122

[22] Filed: Apr. 7, 1980

Related U.S. Application Data

[63] Continuation of Ser. No. 956,351, Oct. 31, 1978, abandoned, which is a continuation of Ser. No. 675,819, Apr. 12, 1976, abandoned.

[30] Foreign Application Priority Data

Apr. 12, 1975 [JP] Japan .................................. 50-48880

[51] Int. Cl.[3] ............................ A61K 9/24; A61K 9/32
[52] U.S. Cl. ........................................ 424/19; 424/20; 424/21; 424/22; 424/32; 424/35
[58] Field of Search .................................. 424/19–22, 424/32, 35, 184

[56] References Cited

U.S. PATENT DOCUMENTS

| Re. 25,205 | 7/1962 | Feinstone | 424/32 |
|---|---|---|---|
| 2,512,192 | 6/1950 | Yen et al. | 424/32 |
| 2,805,977 | 9/1957 | Robinson et al. | 424/32 |
| 2,951,011 | 8/1960 | Feinstone | 424/32 |
| 3,094,464 | 6/1963 | Joullie et al. | 424/35 |
| 3,382,150 | 5/1968 | Grass et al. | 424/31 |
| 3,501,571 | 3/1970 | Yen | 424/184 |
| 3,539,380 | 11/1970 | Johnson | 424/35 |

FOREIGN PATENT DOCUMENTS

| 2149699 | 4/1972 | Fed. Rep. of Germany. | |
| 44-290 | 9/1969 | Japan | 424/31 |
| 46-15639 | 4/1971 | Japan | 424/32 |

OTHER PUBLICATIONS

Chem. Abstracts 77 #9593+(1972) of Casadio, Silvano et al., Ger. Off. 2, 149,699, 13 Apr. 1972, 14 pp.

Primary Examiner—Shep K. Rose
Attorney, Agent, or Firm—Toren, McGeady and Stanger

[57] ABSTRACT

Solid pharmaceutical dosage forms of the sustained release type coated with a coating material composed of an aqueous dispersion of a high molecular weight organopolysiloxane and a water-soluble cellulose derivative in the absence of any organic solvent. The solid dosage forms have an excellent property of highly controllable sustained release in a wide range.

16 Claims, No Drawings

SUSTAINED-RELEASE SOLID PHARMACEUTICAL DOSAGE FORMS AND PREPARATION THEREOF

This is a continuation of application Ser. No. 956,351, filed on Oct. 31, 1978, which, in turn, is a continuation of application Ser. No. 675,819, filed on Apr. 12, 1976, both now abandoned.

BACKGROUND OF THE INVENTION

This invention relates to solid pharmaceutical dosage forms of the sustained-release type and a method of preparing them. More particularly, this invention relates to sustained-release solid dosage forms coated with an aqueous coating dispersion in the absence of an organic solvent and having a releasing time controllable within a wide range.

Various methods have been proposed for the preparation of sustained-release pharmaceutical dosage forms. For example the dosage forms may be coated with a solution of ethyl cellulose and hydroxypropylmethyl cellulose mixed in a certain ratio in an organic solvent to prolong the disintegration time. Another example is where granules of active ingredients are first made, the granules are then divided into a plurality of groups, each of the groups is coated with an organic solvent solution of cellulose acetate phthalate and polyethylene oxide in a ratio different for each of the respective groups to provide a different disintegration time for each group, the thus coated granules are combined from the individual groups in certain proportions, and the combined granules are encapsulated in hard gelatine capsules.

The disadvantage of these prior art methods is the use of organic solvents to make a coating solution which not only is uneconomical but is also susceptible to explosion or fire and contributes to the pollution of the air and the working environment, when the organic solvents are subject to evaporation.

Apart from the above-described prior art techniques, it is known that organopolysiloxanes of a relatively low viscosity or molecular weight, such as, dimethyl silicone fluids, can be used in the preparation of pharmaceutical tablets. In this case, small amounts of the relatively low viscosity organopolysiloxane fluids that are incapable of forming films are added to the tablet-coating solutions which use an organic solvent. This provides a sufficient slipperiness to the surface of the tablets in the coating process as well as a good gloss and slipperiness to the coated finished surfaces. No attempts have been made to use such organopolysiloxane fluids for the purpose of forming films on the surfaces of tablets non especially, for providing the coated tablets with a sustained release property, in which the organopolysiloxane fluids are used in an aqueous dispersion.

The inventors of this invention, noticing the that orally administered organopolysiloxanes produce no adverse effects to the human body and that films of an organopolysiloxane can afford an excellent permeability to low molecular weight materials, have researched on the preparation of pharmaceutical solid dosage forms which should have a satisfactorily sustained release property. During the course of this research work, the inventors initially attempted to coat tablets and granules with an aqueous emulsion of an organopolysiloxane having a sufficient film-formable high molecular weight. This attempt failed due to to the individual tablets or granules becoming too sticky during the coating operation and having too long release time. However, as a result of their further investigation the inventors have discovered that such undesirable stickines and too long release time could be overcome by the inclusion of a water-soluble cellulose derivative to the coating aqueous emulsion. The inventors have also found that the finished product has the excellent property of sustained release of the active ingredients.

SUMMARY OF THE INVENTION

It is therefore an object of this invention to provide a new and improved solid pharmaceutical dosage form of sustained release and a method for the preparation thereof.

Another object of the invention is to provide such method which is characterized by the absence of an organic solvent in the coating process.

The method for preparing sustained release solid dosage forms in accordance with the present invention comprises coating the solid dosage forms with an aqueous emulsion or dispersion containing essentially a high molecular weight organopolysiloxane and a water-soluble cellulose derivative.

Though the resultant coatings on the surfaces of solid dosage forms according to this invention are substantially insoluble, the coatings gradually become porous by the partial dissolution of the water-soluble cellulose derivative in water or in gastric and intestinal fluids, and provides for a gradual release of the active ingredients therethrough into the gastrointestinal tract, so that the rates of release of the active ingredients or the lengths of durability in the activity of the ingredients can freely and easily be controlled within a wide range by varying the composition or the thickness of the coatings.

DETAILED DESCRIPTION OF PREFERRED EMBODIMENTS

The organopolysiloxanes, for example, dimethylpolysiloxanes, methylvinylpolysiloxanes and methylphenylpolysiloxanes, useful in the method of this invention are represented by the average unit formula $R_nSiO_{(4-n)/2}$, where R is a monovalent hydrocarbon group or a hydrogen atom and n is a positive number smaller then 3, and preferably are capable of forming films by themselves. The organopolysiloxanes are linear or branch chained in their molecular structure, wherein the organic groups denoted by R which are bonded to the silicon atoms are saturated or unsaturated monovalent hydrocarbon groups, such as, alkyl (e.g. methyl), alkenyl (e.g. vinyl), aryl (e.g. phenyl), aralkyl (e.g. benzyl) groups and the like. They have a high molecular weight, corresponding to at least 100,000 centistokes of viscosity at 25° C. Also useful are organohydrogenpolysiloxanes which have hydrogen atoms directly bonded to the silicon atoms in place of 50 mole % or less of the above-mentioned organic groups.

The organopolysiloxane or organohydrogenpolysiloxane is preferably curable by crosslinking, if necessary, in the presence of a crosslinking catalyst. The mechanisms for the crosslinking of the polysiloxanes are well known in the silicone technology. For example, organopolysiloxanes with residual hydroxy or alkoxy groups bonded to the silicon atoms are crosslinked by the dehydration or dealcoholation condensation reaction carried out in the presence of an organometallic compound as a catalyst. A mixture of an organohydrogenpolysiloxane and a vinyl-containing organopolysiloxane is also curable by the addition reaction of the silicon-bonded hydrogen atoms Si—H to the vinyl groups in the presence of a platinum catalyst.

The water-soluble cellulose derivatives, the other component useful in the coating dispersion of this invention, are selected from the alkyl, hydroxyalkyl and alkylhydroxyalkyl ethers of cellulose, exemplified by methylcellulose, hydroxyethylcellulose, hydroxypropylcellulose, methylhydroxyethylcellulose, methylhydroxypropylcellulose, ethylhydroxyethylcellulose and the like. Besides these nonionic materials, ionic materials, such as, sodium carboxymethylcellulose and water-soluble salts of hydroxypropyl methylcellulose phthalate and cellulose acetate phthalate, may be used, barring adverse effects. The molecular weights of these cellulose derivatives are not critically restrictive but, preferably, should not be so high that the coating dispersion formed has a viscosity high enough to be an impediment to any subsequent spraying operations.

Next, the aqueous dispersions of the above-described organopolysiloxane and the water-soluble cellulose derivative useful as the coating dispersion in accordance with this invention may be prepared, for example and not limited thereto, by adding an aqueous solution of the cellulose derivative to an emulsion obtained by the emulsification of the organopolysiloxane in the presence of an emulsifier or by emulsion polymerization of one or more hydrolyzable organosilanes, such as alkoxy-containing organosilanes and organopolysiloxanes with low molecular weights including cyclic organopolysiloxanes, such as, octamethyl cyclotetrasiloxane and linear- or branched-chain organopolysiloxanes in the presence of a suitable emulsifier, the method for the emulsion polymerization itself being well known in the silicone technology. Among the methods of preparing the coating dispersions, the most preferred is one by emulsion polymerization, since dispersions with higher homogeneity, which are hardly obtainable by the emulsification of pre-formed high molecular weight organopolysiloxanes, can readily be prepared by this method.

If desired the above coating dispersion may include one or more additives, such as, colorants, flavorings, fillers, lubricants, crosslinking agents, plasticizers, etc., inasmuch as the objects of the present invention are not impaired by the presence of such additives.

Further, in the preparation of the coating dispersion in accordance with this invention, the proportions of the organopolysiloxane and the cellulose derivative may vary depending upon the desired duration of release. It is a rule that when the coating dispersions produce films of the same thickness, larger amounts of the cellulose derivative relative to the organopolysiloxane will work to shorten the release time, while smaller amounts work to prolong the release time. Thus, the ratio of the organopolysiloxane to the cellulose derivative may optionally be chosen in view of the kinds of active ingredients and the desired length of time their effective drug blood concentrations are to be maintained. In general they are in the range of from 5/95 to 95/5 by weight or, preferably, from 20/80 to 95/5.

For the purpose of applying the coating dispersion to the solid dosage forms, any conventional coating equipment may be employed including pan coaters, rotary-drum coaters and fluidizing coaters.

The medical active ingredients, for which sustained release in the human body is desired and which are formed into solid dosage forms in accordance with the present invention, are exemplified by but not limited to the following: antibiotics, such as, penicillin and tetracycline; analgesics, such as, antipyrine and aminopyrine; tranquilizers, such as, chlorpromazine; sedatives, such as, secobarbital and phenobarbital; antipyretics, such as, aspirin and sodium salicilate; diuretics, such as, aminophyline and ammonium chloride; mydriatics, such as, atropin and scopolamine; and sympathomimetic agents, such as, epinephrine and adrenaline.

The present invention will be further described by the following specific examples. In the examples, parts and percentages are all based on weight.

EXAMPLE 1

Preparation of tablets

To a mixture of 50 parts of ammonium chloride and 50 parts of lactose, a solution of 3 parts of polyvinylpyrrolidone (K-30, product of General Aniline & Film Corporation, U.S.A.) in 20 parts of methanol was added with kneading. The resulting mixture was subjected to granulation using an extrusion-type granulator, followed by drying. Immediately after the dried granules were mixed with 0.5 part of magnesium stearate, the mixture was compressed using a rotary tableting machine to form tablets, each tablet being 9 mm in diameter and weighing 300 mg. These tablets were tested for disintegration in accordance with the U.S. Pharmacopeia XIX (USP XIX) and found that their disintegration time was 4 and a half minutes.

Preparation of coating liquids

To "Silicone KM-791," a product of the Shin-Etsu Chemical Co., Japan, i.e., which consists of an aqueous emulsion containing 30% high molecular weight methylvinylpolysiloxane capable of forming films at room temperature, water was added in the amount of two times the weight of the Silicane KM-791, to form a dispersion having a 10% solid content. This dispersion was called "Liquid A."

Apart from the above, hydroxypropyl methylcellulose (EPMC for brevity), having a viscosity of 5.6 centipoise in a 2% aqueous solution at 20° C. (Pharmacoat-606, product of Shin-Etsu Chemical Co., Japan) was dissolved in water to form a solution having a 5% solid content. This solution was called "Liquid B."

Coating

Using Liquids A and B alone or in combination, a coating was applied to the tablets obtained above in a coating pan provided with nozzles for both spraying and hot air blowing to form films of different thicknesses.

The coated tablets were subjected to the dissolution test in accordance with the USP XIX, wherein the dissolution medium was water and the basket was rotated at the rate of 100 r.p.m. During the dissolution test, small portions of water, as the dissolution medium, were taken at certain intervals and analyzed for the chlorineion concentration in order to determine the amount of ammonium chloride dissolved out of the tablet.

TABLE I

| Test No. | 1 | 2 | 3 | 4 | 5 |
|---|---|---|---|---|---|
| Coating liquid | 100% Liquid A | 70% Liquid A + 30% | 50% Liquid A + 50% | 20% Liquid A + 80% | 100% Liquid B |

TABLE I-continued

| | Liquid B | Liquid B | Liquid B | | |
|---|---|---|---|---|---|
| Ratio of methylvinyl polysiloxane and HPMC in coating liquid | 100:0 | 82.5:17.5 | 67:33 | 33:67 | 0:100 |
| Trouble occuring during coating | Too much stickiness to perform coating | None | None | None | None |
| Thickness of film, mm | — | 0.04 | 0.04 | 0.04 | 0.04 |
| % of ammonium chloride released: | | | | | |
| After 30 min. | — | 6.5 | 17 | 35 | 100 |
| After 60 min. | — | 23 | 58 | 100 | — |
| After 90 min. | — | 48 | 100 | — | — |
| After 120 min. | — | 81 | — | — | — |
| After 150 min. | — | 98 | — | — | — |
| After 180 min. | — | 100 | — | — | — |
| Observation | — | (a)* | (b)* | (c)* | (d)* |

*(a) Swelling took place to the tablet in 35 min.; active ingredients dissolved out in 180 min.; film remained complete.
*(b) Swelling took place in 15 min.; active ingredientsdissolved out in 90 min.; film remained complete.
*(c) Swelling took place in 8 min.; active ingredientsdissolved out in 60 min.; film remained complete.
*(d) Total disintegration took place to the tablet in8 min.

EXAMPLE 2

Preparation of tablets

The same as in Example 1.

Preparation of coating liquids

To "Silicone KM-795," a product of the Shin-Etsu Chemical Co., Japan, which consists of an aqueous emulsion containing 30% high molecular weight methylhydrogenpolysiloxane capable of forming films at room temperature water was added in the amount of two times the weight of the Silicane KM-795, to form a dispersion having a 10% solid content. This dispersion was called "Liquid C."

Apart from the above, HPMC having a viscosity of 2.9 centipoise in a 2% aqueous solution at 20° C. (Pharmacoat-603, product of Shin-Etsu Chemical Co., Japan) was dissolved in water to form a solution having a 5% solid content. This solution was called "Liquid D."

The following components:

| Liquid C | 700 parts |
|---|---|
| Liquid D | 400 parts |
| Titanium dioxide | 1 part |
| Amaranth aluminum lake | 2.4 parts |
| Erythrosine aluminum lake | 5.6 parts | were uniformly blended to make a coating liquid. In this coating liquid the ratio of methylhydrogen polysiloxane and HPMC was 71.5 to 28.5.

Coating

The tablets obtained above were coated with the above coating liquid by a fluidizing coater to form films of different thicknesses. No problems occurred during the coating operation.

The coated tablets were subjected to the same dissolution test as in Example 1. The test results are set out in Table II. The films formed remained complete in all of the tests Nos. 6 to 9 after dissolution of the active ingredients.

TABLE II

| Test No. | 6 | 7 | 8 | 9 |
|---|---|---|---|---|
| Thickness of film, mm | 0.04 | 0.06 | 0.08 | 0.15 |
| % of ammonium chloride released: | | | | |
| After 30 min. | 9 | 4 | 2 | 1 |
| After 60 min. | 28 | 19 | 13 | 2 |
| After 90 min. | 62 | 42 | 28 | 9 |
| After 120 min. | 91 | 68 | 50 | 22 |
| After 180 min. | 100 | 92 | 73 | 53 |
| After 240 min. | — | 100 | 100 | 86 |
| After 300 min. | — | — | — | 100 |
| Observation | (e)* | (f)* | (g)* | (h)* |

*(e) Swelling took place to the tablet in 30 min.; active ingredients dissolved out in 180 min.
*(f) Swelling took place in 40 min.; active ingredients dissolved out in 240 min.
*(g) Swelling took place in 55 min.; active ingredients dissolved out in 240 min.
*(h) Swelling took place in 80 min.; active ingredients dissolved out in 300 min.

EXAMPLE 3

Preparation of tablets

A mixture of 99 parts of powdered aspirin and 1 part of corn starch was compressed into tablets by a rotary tableting machine, each tablet being 9 mm in diameter and weighing 300 mg. These tablets were tested for disintegration in accordance with the USP XIX, to find that they were disintegrated in 6 minutes and 20 seconds.

Preparations of coating liquid

Methylcellulose (MC), having a viscosity of 16.5 centipoise in a 2% aqueous solution at 20° C. (Metolose SM-15, product of Shin-Etsu Chemical Co., Japan) was dissolved in water to form a 5% solution. This solution was called "Liquid E."

The following components:

| Liquid C | 750 parts |
|---|---|
| Liquid E | 500 parts |
| Tartrazine | 0.5 parts | were uniformly blended to make a coating liquid for the purpose of this example. In this coating, the ratio of the methylhydrogenpolysiloxane and MC was 75:25 by weight.

Coating

The tablets obtained above were coated with the above coating liquid by the same coating equipment as used in Example 1 to a film thickness of 0.15 mm. No problems occurred during the coating operation.

The coated tablets were subjected to the same dissolution test as in Example 1 (except that the dissolution medium was a simulated gastric fluid). During the test, small portions of the simulated gastric fluid were taken at certain intervals and were analyzed for the total concentration of salicylic acid and aspirin to determine the rate of release of aspirin from the tablet. The test results were as follows.

|  | Rate of release (%) |
| --- | --- |
| After 60 min. | 4 |
| After 120 min. | 25 |
| After 180 min. | 61 |
| After 240 min. | 93 |
| After 300 min | 98 |

What is claimed is:

1. A solid pharmaceutical dosage form of sustained release with a coating layer consisting essentially of an organopolysiloxane curable by crosslinking and a water-soluble ether of cellulose, said organopolysiloxane and said ether of cellulose being present in a ratio of from 5:95 to 95:5 by weight in said coating layer.

2. The solid pharmaceutical dosage form as claimed in claim 1 wherein said organopolysiloxane is represented by the average unit formula $R_nSiO_{(4-n)/2}$ where R is a hydrogen atom or a monovalent hydrocarbon group and n is a positive number smaller than 3.

3. The solid pharmaceutical dosage form as claimed in claim 1 wherein said organopolysiloxane and said ether of cellulose are present in a ratio of from 20:80 to 95:5 by weight in said coating layer.

4. The solid pharmaceutical dosage form as claimed in claim 1 wherein said organopolysiloxane has a viscosity of at least 100,000 centistokes at 25° C.

5. The solid pharmaceutical dosage form as claimed in claim 1 wherein the organic groups bonded to the silicon atoms of said organopolysiloxane are saturated or unsaturated monovalent hydrocarbon groups selected from the group consisting of methyl, vinyl, phenyl and benzyl groups.

6. The solid pharmaceutical dosage form as claimed in claim 1 wherein said organopolysiloxane is a methylvinylpolysiloxane.

7. The solid pharmaceutical dosage form as claimed in claim 1 wherein said organopolysiloxane is a methylhydrogenpolysiloxane.

8. The solid pharmaceutical dosage form as claimed in claim 1 wherein said organopolysiloxane is a methylphenylpolysiloxane.

9. The solid pharmaceutical dosage form as claimed in claim 1 wherein said water-soluble ether of cellulose is a hydroxypropylmethylcellulose.

10. The solid pharmaceutical dosage form as claimed in claim 1 wherein said water-soluble ether of cellulose is a methylcellulose.

11. The dosage form of claim 1 wherein the organopolysiloxane has the average unit formula $R_nSiO_{(4-n)/2}$ wherein R is a monovalent hydrocarbon selected from the group consisting of alkyl, aryl, alkenyl and aralkyl or hydrogen and n is a positive number smaller than 3.

12. The dosage form of claim 11 wherein R is methyl, vinyl or phenyl.

13. The dosage form of claim 11 wherein the water-soluble ether is selected from the group consisting of alkyl, hydroxyalkyl, and alkylhydroxyalkyl ethers of cellulose.

14. The dosage form of claim 11 wherein the ether of cellulose is selected from the group consisting of methylcellulose, hydroxyethylcellulose, hydroxypropylcellulose, methylhydroxyethylcellulose, methylhydroxypropylcellulose, ethylhydroxyethylcellulose.

15. The dosage form of claim 11 wherein the organopolysiloxane has a viscosity of at least 100,000 centistokes at 25° C.

16. Method for preparing a sustained release solid pharmaceutical dosage form comprising coating said dosage form with an aqueous dispersion consisting essentially of an organopolysiloxane and a water-soluble ether of cellulose, said organopolysiloxane and said ether of cellulose being present in a ratio of from 5:95 to 95:5 by weight in said coating layer.

* * * * *

UNITED STATES PATENT OFFICE
CERTIFICATE OF CORRECTION

Patent No. 4,268,496        Dated May 19, 1981

Inventor(s) Shigeru Ohno and Fujio Sekigawa

It is certified that error appears in the above-identified patent and that said Letters Patent are hereby corrected as shown below:

In the heading of the patent [30] should read as follows:

[30]    Foreign Application Priority Data

April 22, 1975     Japan......50-48880

*Signed and Sealed this*

*First* Day of *September 1981*

[SEAL]

*Attest:*

GERALD J. MOSSINGHOFF

*Attesting Officer*      *Commissioner of Patents and Trademarks*